United States Patent

Suzuki et al.

[11] Patent Number: 5,126,341
[45] Date of Patent: Jun. 30, 1992

[54] ANTI-INFLAMMATORY 1,8-NAPHTHYRIDIN-2-ONE DERIVATIVES

[75] Inventors: Fumio Suzuki, Mishima; Takeshi Kuroda, Shizuoka; Kenji Ohmori, Mishima; Tadafumi Tamura; Hisashi Hosoe, both of Shizuoka, all of Japan

[73] Assignee: Kyowa Hakko Kogyo Co., Ltd., Tokyo, Japan

[21] Appl. No.: 684,214

[22] Filed: Apr. 12, 1991

[30] Foreign Application Priority Data

Apr. 16, 1990 [JP] Japan ................. 2-100006

[51] Int. Cl.⁵ .................. A61K 31/435; C07D 471/04
[52] U.S. Cl. .................. 514/234.5; 514/253; 514/256; 514/275; 514/300; 544/127; 544/328; 544/331; 544/362; 544/405; 546/123
[58] Field of Search .................. 546/123; 544/127, 328, 544/331, 362, 405; 514/234.5, 253, 256, 275, 300

[56] References Cited

U.S. PATENT DOCUMENTS 4,264,602  4/1961  Hardtmann .................. 546/123

Primary Examiner—Bernard Dentz
Attorney, Agent, or Firm—Fitzpatrick, Cella, Harper & Scinto

[57] ABSTRACT

Disclosed are naphthyridine derivatives represented by formula (I)

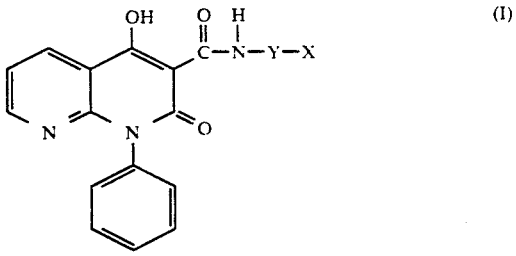

wherein:

X represents hydrogen; lower alkyl; aralkyl; substituted or unsubstituted aryl; substituted or unsubstituted aromatic heterocyclic group; $-NR^1R^2$ wherein $R^1$ and $R^2$ independently represent hydrogen or lower alkyl;

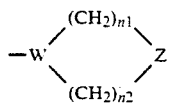

wherein W represents N or CH, Z represents a single bond, oxygen or $NR^3$ (wherein $R^3$ represents hydrogen, lower alkyl or benzyl) and n1 and n2 represent an integer of 1 to 3; or substituted or unsubstituted thiazolinyl; and Y is a single bond or alkylene and pharmaceutically acceptable salts thereof. The compounds show potent anti-inflammatory activity and are expected to be useful in treating rheumarthritis.

3 Claims, No Drawings

ANTI-INFLAMMATORY 1,8-NAPHTHYRIDIN-2-ONE DERIVATIVES

BACKGROUND OF THE INVENTION

The present invention relates to novel 1,8-naphthyridin-2-one derivatives having an anti-inflammatory activity and which are useful for the treatment of rheumarthritis.

Rheumarthritis, which is characterized by inflammation and pain of articulations, shows a morbidity rate of 3–4%. While pathogenesis of rheumarthritis is not fully clarified, steroid type and non-steroid type anti-inflammatory agents have been used for therapy of rheumarthritis. In contrast to other non-steroid type anti-inflammatory agents, piroxicam (U.S. Pat. No. 3,591,584) and RU-43526 [J. Med. Chem., 31, 1453 (1988)] have no carboxylic acid moiety.

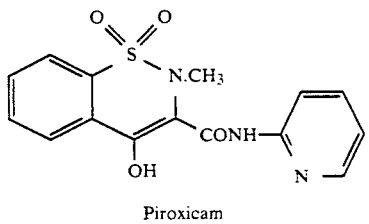

Piroxicam

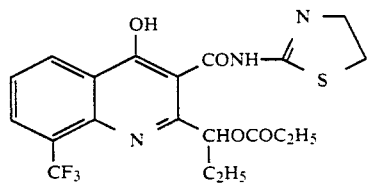

RU-43526

As to 4-hydroxy-1,8-naphthyridin-2-one derivatives, the following compounds represented by formula (A) are disclosed.

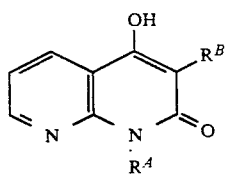

(1) A compound of formula (A) wherein $R^A$ is phenyl and $R^B$ is nitro having anti-allergic activity (Japanese Published Unexamined Patent Application No. 36694/77).

(2) A compound of formula (A) wherein $R^A$ is phenyl and $R^B$ is butyl having anti-ulcer activity (Sch 12223) [J Pharm. Exp. Ther., 246, 578 (1988)].

(3) Compounds of formula (A) wherein $R^A$ is alkyl, aralkyl, or the like and $R^B$ is carbamoyl, N-alkylcarbamoyl, N-alkoxycarbamoyl, or the like having anti-ulcer activity (U S. Pat. No. 4,215,123).

(4) Compounds of formula (A) wherein $R^A$ is alkyl or the like and $R^B$ is ethoxycarbonyl [J. Med. Chem., 30, 2270, (1987)].

SUMMARY OF THE INVENTION

An object of the present invention is to provide novel naphthyridine derivatives having potent anti-inflammatory activity.

The present invention relates to naphthyridine derivatives represented by general formula (I):

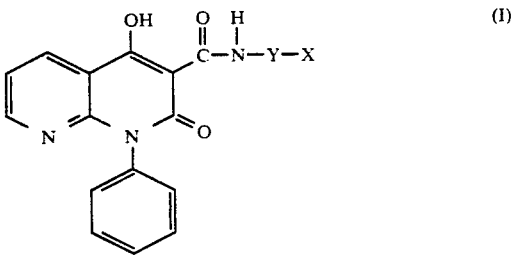

wherein X represents hydrogen; lower alkyl; aralkyl; substituted or unsubstituted aryl; substituted or unsubstituted aromatic heterocyclic group; —$NR^1R^2$ wherein $R^1$ and $R^2$ independently represent hydrogen or lower alkyl;

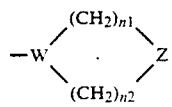

wherein W represents N or CH, Z represents a single bond, oxygen or $NR^3$ (wherein $R^3$ represents hydrogen, lower alkyl or benzyl), and n1 and n2 represent an integer of 1 to 3 or substituted or unsubstituted thiazolinyl; and Y is a single bond or alkylene and pharmaceutically acceptable salts thereof.

The compounds represented by formula (I) are hereinafter referred to as Compounds (I); the same applies to the compounds of other formula numbers.

DETAILED DESCRIPTION OF THE INVENTION

In the definitions of the groups in formula (I), the lower alkyl means a straight-chain or branched alkyl group having 1 to 6 carbon atoms, for example, methyl, ethyl, propyl, isopropyl, butyl, isobutyl, sec-butyl, tert-butyl, pentyl, neopentyl and hexyl. The aralkyl means an aralkyl group having 7 to 20 carbon atoms, for example, benzyl, phenethyl, benzhydryl and trityl. The aryl means an aryl group having 6 to 10 carbon atoms such as phenyl and naphthyl. Examples of the aromatic heterocyclic group include pyridyl, pyrimidinyl, thiazole and benzothiazole. The alkylene means a straight-chain or branched alkylene group having 1 to 6 carbon atoms such as methylene, ethylene, trimethylene, tetramethylene, pentamethylene, hexamethylene, ethylethylene and propylene. The aryl, the aromatic heterocyclic group and the thiazolinyl may be substituted by 1 to 2 substituents which are the same or different. Examples of the substituents are lower alkyl, lower alkoxy, halogen, nitro, and amino. The lower alkyl and the alkyl moiety in the lower alkoxy are the same as defined for the lower alkyl described above. Examples of the halogen include fluorine, chlorine, bromine and iodine.

The pharmaceutically acceptable salts of Compounds (I) include acid addition salts, metal salts, ammonium salts, organic amine addition salts, and amino acid addition salts.

As the pharmaceutically acceptable acid addition salts of Compounds (I), inorganic acid addition salts such as hydrochloride, sulfate and phosphate, and organic acid addition salts such as acetate, maleate, fumarate, tartrate and citrate may be mentioned. As the pharmaceutically acceptable metal salts, alkali metal salts such as sodium salt and potassium salt, alkaline earth metal salts such as magnesium salt and calcium salt, aluminum salt, and zinc salt may be mentioned. As the pharmaceutically acceptable organic amine addition salts, salts with morpholine and piperidine may be mentioned, and as the pharmaceutically acceptable amino acid addition salts, salts with lysine, glycine and phenylalanine may be mentioned.

The processes for preparing Compounds (I) are described below.

In the following processes, in cases where the defined groups change under the conditions shown or are inappropriate for practicing the processes, the processes can be readily carried out by applying thereto means conventionally used in organic synthetic chemistry, for example, protection of functional groups and elimination of protecting groups.

Process 1

Compound (I) can be obtained by allowing Compound (II) to react with Compound (III), if necessary, in the presence of a base.

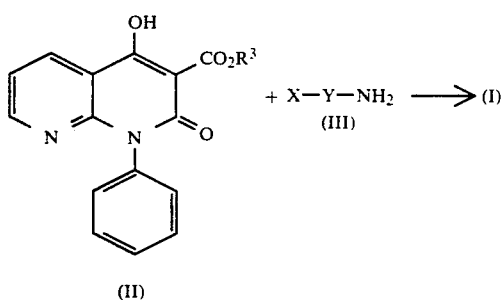

In the above formulae, $R^3$ represents lower alkyl; and X and Y have the same significances as defined above.

The lower alkyl in formula (II) has the same significance as the lower alkyl described above.

Examples of the base are alkali metal carbonates such as potassium carbonate and sodium carbonate, alkali metal hydrides such as sodium hydride, alkali metal alkoxides such as sodium methoxide and sodium ethoxide, and alkylamines such as triethylamine.

As a reaction solvent, those which are inert to the reaction, for example, ethers such as tetrahydrofuran and dioxane, amides such as dimethylformamide, alcohols such as methanol and ethanol, hydrocarbons such as xylene, toluene, hexane and cyclohexane, halogenated hydrocarbons such as chloroform and carbon tetrachloride, and dimethylsulfoxide may be used alone or in combination.

The reaction is carried out at 0° to 300° C. and is completed in 10 minutes to 24 hours.

Compound (II) can be obtained in accordance with the following reaction steps shown as Processes A and B.

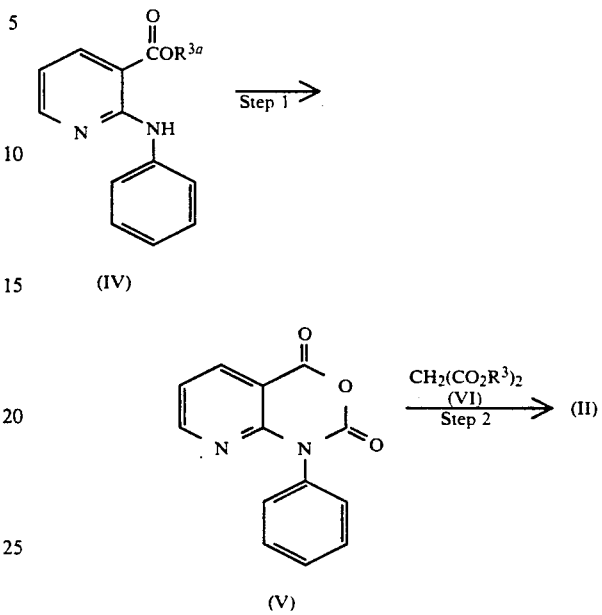

In the above formulae, $R^3$ has the same significance as defined above; and the definition of $R^{3a}$ is the same as $R^3$.

The starting Compound (IV) can be synthesized by a known method [J. Org. Chem., 39, 1803 (1974)] or by its modification.

Step 1

Compound (V) can be obtained by allowing Compound (IV) to react with phosgene, triphosgene or trichloromethyl chloroformate (TCF), if necessary, in a solvent.

As the reaction solvent, those which are inert to the reaction, for example, ethers such as tetrahydrofuran and dioxane, hydrocarbons such as toluene and hexane, and halogenated hydrocarbons such as 1,2-dichloroethane and chloroform may be used alone or in combination.

The reaction is carried out at 0° to 200° C. and is completed in 5 minutes to 24 hours.

Step 2

Compound (II) can be obtained by allowing Compound (V) to react with Compound (VI), in the presence of a base, and if necessary, in a solvent.

The reaction is carried out under the same conditions using the same solvent and base as in Step 1.

Process B

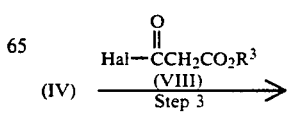

(IV) $\xrightarrow[\text{Step 3}]{\text{Hal—CCH}_2\text{CO}_2R^3 \\ \text{(VIII)}}$ -continued
Process B

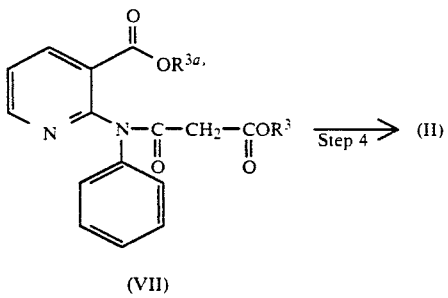

(VII)

In the above formulae, Hal represents chlorine, bromine or iodine; and $R^3$ and $R^{3a}$ have the same significances as defined above.

Step 3

Compound (VII) can be obtained by allowing Compound (IV) to react with Compound (VIII) in the presence of a base, and if necessary, in a solvent.

The reaction is carried out under the same conditions using the same solvent and base as in Step 1.

Step 4

Compound (II) can be obtained by treating Compound (VII) with a base, if necessary, in a solvent.

The reaction is carried out under the same conditions using the same solvent and base as in Step 1.

Process 2

Compound (I) can also be obtained by the following reaction steps.

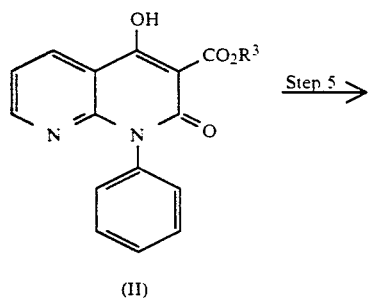

(II)

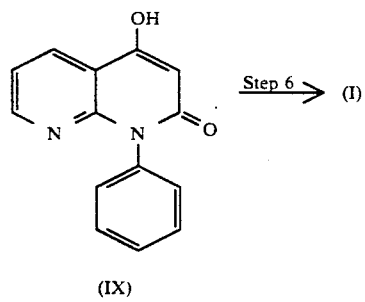

(IX)

In the above formulae, $R^3$ has the same significance as defined above.

Step 5

Compound (IX) can be obtained by heating Compound (II) in a solvent in the presence of an alkali.

As the alkali, alkali metal hydroxides such as sodium hydroxide, alkali metal carbonates such as potassium carbonate, alkali metal bicarbonates such as potassium bicarbonate, etc. may be used.

As the reaction solvent, water, alcohols such as methanol and ethanol, ethers such as tetrahydrofuran and dioxane, etc. may be used alone or in combination.

The reaction is carried out at 30° to 200° C. and is completed in 5 minutes to 24 hours.

Step 6

Compound (I) can be obtained by allowing Compound (IX) to react with Compound (X) represented by formula (X):

$$X-Y-N=C=O \quad (X)$$

(wherein X and Y have the same significances as defined above), if necessary, in the presence of a base.

The reaction is carried out under the same conditions using the same solvent and base as in Process 1.

Process 3

Compound (I) can also be prepared according to the following reaction step.

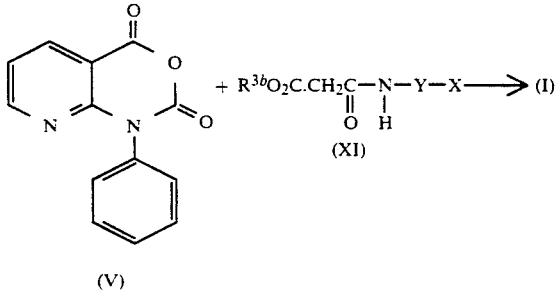

In the above formula, the definition of $R^{3b}$ is the same as $R^3$; and X and Y have the same significances as defined above.

Compound (I) can be obtained by allowing Compound (V) to react with Compound (XI) in the presence of a base.

The reaction is carried out under the same conditions using the same solvent and base as in Process 1.

The intermediates and the desired products in the processes described above can be isolated and purified by purification means conventionally used in organic synthetic chemistry, for example, filtration, extraction, washing, drying, concentration, recrystallization and various kinds of chromatography. The intermediates can be subjected to the subsequent reaction without particular purification.

In the case where a salt of Compound (I) is desired and it is produced in the form of the desired salt, it can be subjected to purification as such. In the case where Compound (I) is produced in the free state and its salt is desired, it can be converted into its salt in a conventional manner.

Compounds (I) and pharmaceutically acceptable salts thereof sometimes exist in the form of an addition product with water or with a solvent. Such addition products are also included within the scope of the present invention.

Specific examples of Compounds (I) are shown in Table 1. The compound numbers in the table respectively correspond to the numbers of Examples described below.

TABLE 1
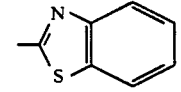
| Compound No. | —Y—X |
|---|---|
| 1 | —(CH$_2$)$_3$CH$_3$ |
| 2 | —CH$_3$ |
| 3 |  |
| 4 | 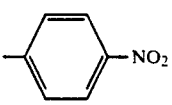 |
| 5 | 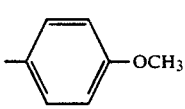 |
| 6 | —N(CH$_3$)$_2$ |
| 7 | —CH$_2$CH$_2$N(CH$_3$)$_2$ |
| 8 | 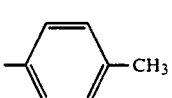 |
| 9 |  |
| 10 | 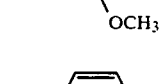 |
| 11 | 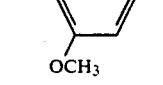 |
| 12 | 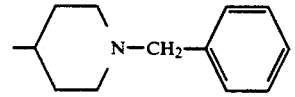 |
TABLE 1-continued
| Compound No. | —Y—X |
|---|---|
| 13 |  |
| 14 | (4-Cl-phenyl) |
| 15 | (4-NO$_2$-phenyl) |
| 16 | (4-OCH$_3$-phenyl) |
| 17 | (4-CH$_3$-phenyl) |
| 18 | (3-OCH$_3$-phenyl) |
| 19 | (2-OCH$_3$-phenyl) |
| 20 | (phenyl) |
| 21 | (4-benzylpiperidinyl) |
| 22 | (thiazoline) |
| 23 | (pyrazine) |

TABLE 1-continued

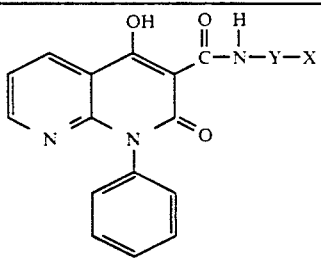

| Compound No. | —Y—X |
|---|---|
| 24 | (thiazole with C2H5, S, N-N) |
| 25 | (pyridine with OCH3) |
| 26 | (pyridine with Cl) |
| 27 | —N(morpholine)O |
| 28 | —CH2—(pyridine) |
| 29 | —CH2—(pyridine) |
| 30 | (phenyl with NH2) |
| 31 | (pyridine with CH3) |
| 32 | (pyridine) |

The pharmacological activities of Compounds (1) are illustrated below.

a) Effect on carrageenin-induced paw edema

Male Wistar rats weighing 150 to 160 g (n=3-5) were used in the experiment. After the right hind paw volume was measured with the plethysmograph (TK-101; Unicom Co., Ltd.), the test compound (100 mg/kg) was orally administered. After one hour, 0.1 ml of 1 % carrageenin (λ-carrageenin; PICNIN-A ®, Zushi Kagaku Co., Ltd.) was subcutaneously injected into the right hind paw footpad. Three hours after the injection of carrageenin, the right hind paw volume was measured and the swelling rate was determined by the following equation 1.

$$\text{Swelling rate } (\%) = \frac{Vt - Vo}{Vo} \times 100 \quad (1)$$

Vt: the right hind paw volume measured 3 hours after the injection of carrageenin Vo: the right hind paw volume measured prior to the injection of carrageenin The suppression rate was calculated by the following equation 2.

$$\text{Suppression rate } (\%) = \frac{Swc - Swt}{Swc} \times 100 \quad (2)$$

Swt: the swelling rate of the group administered with the test compound

Swc: the swelling rate of the control group administered with no test compound

The results are shown in Table 2.

b) Effect on zymosan-induced paw edema

The experiment was carried out in the same manner as in the carrageenin-induced paw edema test except that 1% zymosan (Zymosan A ®; Sigma Chemical Co.) was used in place of 1% carrageenin and the right hind paw volume was measured 4 hours after the injection of the edema-inducing substance instead of 3 hours. The swelling rate and the suppression rate were calculated by equation 1 and equation 2, respectively. The results are shown in Table 2.

c) Arachidonic acid-induced paw edema

The experiment was carried out in the same manner as in the carrageenin-induced paw edema test except that 0.5% arachidonic acid was used in place of 1% carrageenin and the right hind paw volume was measured one hour after the injection of the edema-inducing substance instead of 3 hours. The swelling rate and the suppression rate were calculated by equation 1 and equation 2, respectively. The results are shown in Table 2.

TABLE 2

| | Suppression rate for paw swelling (%) | | |
|---|---|---|---|
| | (a) Carrageenin-induced edema | (b) Zymosan-induced edema | (c) Arachidonic acid-induced edema |
| Compound | | | |
| 1 | | 20.5 | |
| 4 | 40.0 | 37.8 | 34.9 |
| 5 | 38.5 | 38.4 | 48.0 |
| 6 | 31.7 | 27.3 | |
| 7 | 23.2 | | |
| 9 | 25.2 | | |
| 19 | 34.2 | | |
| 22 | | | 33.4 |
| 23 | 22.7 | 22.2 | |
| 28 | 27.3 | | 41.6 |
| 29 | | | 33.3 | d) Effect on Type III allergic reaction-induced pleurisy

1. Preparation of IgG fraction of rabbit anti-egg white albumin (anti-OA)

IgG was purified from rabbit anti-OA serum prepared in advance by the method of Koda et al. [Folia Pharmacol., Japon 66, 237, (1970)] in the following manner.

A saturated solution of ammonium sulfate (half volume of the serum) was added to the anti-OA serum, and the mixture was left for one hour at 4° C. The precipitate was taken by centrifugation (3,000 rpm, 30 min, 4° C.) and dissolved in phosphate buffered saline of Dulbecco. Then, ammonium sulfate fractionation was carried out three times in the same manner as above, whereby a purified IgG fraction was obtained.

2. Type III allergic reaction-induced pleurisy

Male Wistar rats weighing 225-250 g were pre-bred for several days and fasted overnight prior to the experiment. The test compound (100 mg/kg) was orally administered to the animals, and after 30 minutes, IgG of rabbit anti-OA (0.2 ml, 5 mg protein/ml) was injected into the pleural cavity of the animals under anesthesia with ether. Thirty minutes after the injection of IgG, OA (albumin egg grade III; Sigma Chemical Co.) was intravenously injected into the animals as an inducer of pleurisy. After two hours, Evans Blue (25 mg/kg) was intravenously injected, and four and a half hours after the induction of pleurisy, the animals were killed by bleeding.

Then, an exudate in the pleural cavity was obtained, and the volume of the exudate was measured. The pleural cavity was rinsed with 5 ml of physiological saline and the rinsings were added to the exudate. The number of infiltrated cells in the mixture was counted and the volume of the dye in the mixture was determined by the absorption at 625 nm [Agent Actions., 25, 326 (1988)]. The suppression rates for the volume of the exudate, the number of infiltrated cells and the volume of the dye in the pleural cavity were calculated by the following equation 3.

$$\text{Suppression rate (\%)} = 100 - \frac{S \cdot V - N \cdot V}{P \cdot V - N \cdot V} \times 100 \quad (3)$$

S.V: the value obtained with the group administered with the test compound and in which pleurisy is induced N.V: the value obtained with the group in which pleurisy is not induced P.V: the value obtained with the group administered with no test compound and in which pleurisy is induced The results are shown in Table 3

TABLE 3

| | Suppression rate (%) | | |
|---|---|---|---|
| Compound | Volume of exudate | Volume of dye in the exudate | Number of infiltrated cells in the exudate |
| 2 | 27.2 | 28.3 | |
| 4 | 75.3 | 54.4 | 30.5 |
| 5 | 100.0 | 66.5 | 58.6 |
| 8 | | | 21.7 |
| 9 | 27.3 | | 28.5 |
| 11 | 22.1 | 37.2 | |
| 12 | | 24.0 | |
| 13 | 28.9 | 25.8 | |
| 16 | | | 25.4 |
| 17 | 22.4 | | 21.5 |
| 18 | 26.9 | | 22.1 |

TABLE 3-continued

| | Suppression rate (%) | | |
|---|---|---|---|
| Compound | Volume of exudate | Volume of dye in the exudate | Number of infiltrated cells in the exudate |
| 19 | | | 26.8 |
| 21 | 32.4 | 50.2 | 22.1 |
| 22 | 89.2 | 51.0 | 34.6 |
| 23 | 24.0 | 43.2 | 26.7 |
| 24 | 29.7 | 32.1 | |
| 27 | | 23.6 | | e) Acute toxicity

The test compounds were orally or intraperitoneally administered to male dd-mice weighing 20 to 25 g. MLD (Minimum Lethal Dose) was determined by observing the mortality for seven days after the administration.

The results are shown in Table 4.

TABLE 4

| | Acute toxicity (MLD: mg/kg) | |
|---|---|---|
| Compound | p.o. | i.p. |
| 4 | >300 | >100 |
| 5 | 300 | >100 |
| 6 | >300 | >100 |
| 7 | >300 | >100 |
| 9 | >300 | >100 |
| 11 | >300 | >100 |
| 19 | >300 | >100 |
| 22 | >300 | >100 |
| 23 | >300 | >100 |
| 28 | >300 | >100 |
| 29 | >300 | >100 |

It is considered that the tissue disturbance caused by immunocomplex (Type III allergy reaction) is one of the pathogenetic factors for rheumarthritis. Hence, the above results suggest that Compounds (I) will be effective for the therapy of rheumarthritis by the suppression effects on both inflammation and Type III allergic reaction.

Compounds (I) and pharmaceutically acceptable salts thereof may be used as they are or in various preparation forms. The pharmaceutical composition of the present invention can be prepared by uniformly mixing Compound (I) or a pharmaceutically acceptable salt thereof as the active ingredient in an effective amount, with pharmaceutically acceptable carriers. These pharmaceutical compositions are desirably in a single dose unit which is suited for oral or parenteral administration.

In preparing the composition for oral administration, any pharmaceutically acceptable carriers may be used according to the preparation form. For example, liquid preparations such as a suspension and a syrup may be prepared using water; sugars such as sucrose, sorbitol and fructose; glycols such as polyethylene glycol and propylene glycol; oils such as sesame oil, olive oil and soybean oil; preservatives such as p-hydroxybenzoic acid esters; flavors such as strawberry flavor and peppermint, etc. Powders, pills, capsules and tablets may be prepared using excipients such as lactose, glucose, sucrose and mannitol; disintegrators such as starch and sodium alginate; lubricants such as magnesium stearate and talc; binders such as polyvinyl alcohol, hydroxypropyl cellulose and gelatin; surfactants such as fatty acid esters; plasticizers such as glycerine, etc. Tablets and capsules are the most useful single dose units for oral administration since their administration is easy.

A solution for parenteral administration may be prepared using carriers such as distilled water, a saline solution, a glucose solution, and a mixture of a saline solution and a glucose solution.

The effective dose and the administration schedule of Compounds (I) or pharmaceutically acceptable salts thereof vary depending upon mode of administration, age, body weight and conditions of a patient, etc., but it is generally preferred to administer the effective compound in a dose of 1 to 1,000 mg/person/day atone time or in 2 to 3 parts.

Certain embodiments of the invention are illustrated in the following examples.

EXAMPLE 1

N-(n-Butyl)-4-hydroxy-2-oxo-1-phenyl-1H-1,8-naphthyridine-3-carboxamide (Compound 1)

Xylene (30 ml) was added to 7.5 g (0.0051 mol) of Compound IIa obtained in Reference Example 2 and 0.27 ml (0.015 mol) of n-butylamine, and the mixture was heated to reflux for 2 hours. The resulting solution was cooled to room temperature and the precipitate was taken by filtration. After 150 ml of ethyl acetate was added to the precipitate and the mixture was stirred for one hour, the resulting crystals were taken by filtration. Recrystallization from ethanol-water gave 1.1 g (yield 62%) of Compound 1 as colorless crystals.

Melting point: 181–184° C. (ethanol-water)
MS (EI) m/e: 337(M+), 294, 265
NMR (CF$_3$COOD) δ (ppm): 9.40(1H, dd, J=8, 2 Hz), 8.62 (1H, dd, J=4, 2 Hz), 7.75–7.96(4H, m), 7.43–7.62 (2H, m). 3.63(2H, t, J=7 Hz), 1.65–1.84(2H, m), 1.40–1.57(2H, m), 1.04(3H, t, J=7 Hz)
IR (KBr) cm$^{-1}$: 1622, 1554
Elemental analysis (%): C$_{19}$H$_{19}$N$_3$O$_3$
Calcd. C 67.64, H 5.67, N 12.45.
Found C 67.83, H 5.96, N 12.40.

EXAMPLE 2

4-Hydroxy-N-methyl-2-oxo-1-phenyl-1H-1,8-naphthyridine-3-carboxamide (Compound 2)

Compound 2 was obtained in the same manner as in Example 1 except for the use of methylamine instead of n-butylamine (yield 70%).

Melting point: >300° C. (ethanol)
MS (EI) m/e: 295(M+), 294, 263, 168
NMR (CF$_3$COOD) δ (ppm): 9.40(1H, dd, J=8, 2 Hz), 8.63 (1H, dd, J=6, 2 Hz), 7.73–7.94(4H, m), 7.45–7.58 (2H, m)
IR (KBr) cm$^{31\ 1}$: 1629, 1595, 1553
Elemental analysis (%): C$_{16}$H$_{13}$N$_3$O$_3$
Calcd.: C 65.08, H 4.44, N 14.23.
Found : C 65.29, H 4.26, N 14.184.

EXAMPLE 3

N-Benzyl-4-hydroxy-2-oxo-1-phenyl-1H-1,8-naphthyridine-3-carboxamide (Compound 3)

Compound 3 was obtained in the same manner as in Example 1 except for the use of benzylamine instead of n-butylamine (yield 66%).

Melting point: 219–222° C. (dimethylsulfoxide-water)
MS (EI) m/e: 371(M+), 265
NMR (CF$_3$COOD) δ (ppm): 9.40(1H, dd, J=8, 2 Hz), 8.63 (1H, dd, J=4, 2 Hz), 7.90(1H, dd, J=8, 4 Hz), 7.75–7.86(3H, m), 7.46–7.58(2H, m), 7.30–7.46 (5H, m), 4.77(2H, s)
IR (KBr) cm$^{-1}$: 1627, 1582, 1549
Elemental analysis (%): C$_{22}$H$_{17}$N$_3$O$_3$
Calcd.: C 71.15, H 4.61, N 11.31.
Found: C 71.54, H 4.62, N 11.22.

EXAMPLE 4

4-Hydroxy-2-oxo-1-phenyl-N-(3-pyridyl)-1H-1,8-naphthyridine-3-carboxamide (Compound 4)

Compound 4 was obtained in the same manner as in Example 1 except for the use of 3-aminopyridine instead of n-butylamine (yield 74%).

Melting point: >300° C. (dimethylsulfoxide)
MS (EI) m/e: 358(M+), 265, 94
NMR (CF$_3$COOD) δ (ppm): 9.76(1H, d, J=2 Hz), 9.47(1H, dd, J=8, 2 Hz), 8.88–8.93(1H, m), 8.74(1H, dd, J=6, 2 Hz), 8.67(1H, d, J=6 Hz), 8.16(1H, dd, J=8, 6 Hz), 7.90(1H, dd, J=8, 6 Hz), 7.75–7.92(3H, m), 7.53–7.57(2H, m)
IR (KBr) cm$^{-1}$: 1658, 1620, 1542
Elemental analysis (%): C$_{20}$H$_{14}$N$_4$O$_3$.0.3H$_2$O
Calcd.: C 66.04, H 4.05, N 15.40.
Found: C 66.21, H 3.92, N 15.16.

EXAMPLE 5

4-Hydroxy-2-oxo-1-phenyl-N-(4-pyridyl)-1H-1,8-naphthyridine-3-carboxamide (Compound 5)

Compound 5 was obtained in the same manner as in Example 1 except for the use of 4-aminopyridine instead of n-butylamine (yield 51%).

Melting point: >300° C. (dimethylsulfoxide)
MS (EI) m/e: 358M+), 357, 265, 263
NMR (CF$_3$COOD) δ (ppm): 9.47(1H, d, J=8 Hz), 8.75(1H, d, J=6 Hz), 8.70(2H, d, J=7 Hz), 8.53(2H, d, J=7 Hz), 7.99(1H, dd, J=8, 6 Hz), 7.79–7.93(3H, m), 7.49–7.59(2H, m)
IR (KBr) cm$^{-1}$: 1687, 1589, 1503
Elemental analysis (%): C$_{20}$H$_{14}$N$_4$O$_3$.0.6H$_2$O
Calcd.: C 65.07, H 4.15, N 15.17.
Found: C 65.22, H 3.85, N 14.93.

EXAMPLE 6

N-Dimethylamino-4-hydroxy-2-oxo-1-phenyl-1H-1,8-naphthyridine-3-carboxamide (Compound 6)

Compound 6 was obtained in the same manner as in Example 1 except for the use of N,N-dimethylhydrazine instead of n-butylamine (yield 57%).

Melting point: 239–240° C. (isopropyl alcohol-water)
MS (EI) m/e: 324(M+), 265, 263
NMR (CDCl$_3$) δ (ppm): 17.36(1H, s), 10.74(1H, s), 8.51–8.59(2H, m), 7.49–7.64(3H, m), 7.20–7.32 (3H, m), 2.67(6H, s)
IR (KBr) cm$^{-1}$: 1626, 1548
Elemental analysis (%): C$_{17}$H$_{16}$N$_4$O$_3$
Calcd.: C 62.95, H 4.97, N 17.27.
Found: C 63.19, H 5.01, N 17.09.

EXAMPLE 7

N-(2-Dimethylaminoethyl)-4-hydroxy-2-oxo-1-phenyl-1H-1,8-naphthyridine-3-carboxamide (Compound 7)

Compound 7 was obtained in the same manner as in Example 1 except for the use of N,N-dimethylaminoethylamine instead of n-butylamine (yield 66%).

Melting point: 240–242° C. (ethanol)
MS (EI) m/e: 352(M+), 265, 58

NMR (CDCl₃) δ (ppm): 17.50–17.77(1H, brs), 10.09(1H, brs), 8.49–8.56(2H, m), 7.47–7.62(3H, m), 7.21–7.29(3H, m), 3.50–3.58(2H, m), 2.47–2.52(2H, m), 2.25(6H, s)

IR (KBr) cm⁻¹: 1657, 1627
Elemental analysis (%): $C_{19}H_{20}N_4O_3$
Calcd.: C 64.76, H 5.72, N 15.90.
Found: C 64.41, H 5.87, N 15.50.

EXAMPLE 8

N-(3-Chlorophenyl)-4-hydroxy-2-oxo-1-phenyl-1H-1,8-naphthyridine-3-carboxamide (Compound 8)

Compound 8 was obtained in the same manner as in Example 1 except for the use of 3-chloroaniline instead of n-butylamine (yield 75%).

Melting point: 295–298° C. (dimethylsulfoxide-water)
MS (EI) m/e: 391, 393(M⁺), 265
NMR (CF₃COOD) δ (ppm): 9.43(1H, dd, J=8, 2 Hz), 8.69 (1H, dd, J=6, 2 Hz), 7.95(1H, dd, J=8, 6 Hz), 7.81–7.88(3H, m), 7.64(1H, s), 7.52–7.59(2H, m), 7.31–7.43(3H, m)
IR (KBr) cm⁻¹: 1660, 1592, 1538
Elemental analysis (%): $C_{21}H_{14}ClN_3O_3$
Calcd.: C 64.38, H 3.60, N 10.72.
Found: C 64.31, H 3.16, N 10.50.

EXAMPLE 9

4-Hydroxy-N-(3-methylphenyl)-2-oxo-1-phenyl-1H-1,8-naphthyridine-3-carboxamide (Compound 9)

Compound 9 was obtained in the same manner as in Example 1 except for the use of m-toluidine instead of n-butylamine (yield 74%).

Melting point: 230–299° C. (dimethylsulfoxide-water)
MS (EI) m/e: 371(M⁺), 265, 107
NMR (CF₃COOD) δ (ppm): 9.43(1H, dd, J=8, 2 Hz), 8.69 (1H, dd, J=6, 2 Hz), 7.94(1H, dd, J=8, 6 Hz), 7.80–7.88(3H, m), 7.53–7.59(2H, m), 7.20–7.40 (4H, m), 2.41(3H, s)
IR (KBr) cm⁻¹: 1660, 1621, 1563
Elemental analysis (%): $C_{22}H_{17}N_3O_3$
Calcd.: C 71.15, H 4.61, N 11.31.
Found: C 71.42, H 4.43, N 11 32.

EXAMPLE 10

4-Hydroxy-N-(2-methylphenyl)-2-oxo-1-phenyl-1H-1,8-naphthyridine-3-carboxamide (Compound 10)

Compound 10 was obtained in the same manner as in Example 1 except for the use of o-toluidine instead of n-butylamine (yield 74%).

Melting point: 280–283° C. (dimethylsulfoxide-water)
MS (EI) m/e: 371(M⁺), 265, 107
NMR (CF₃COOD) δ (ppm): 9.44(1H, dd, J=8, 2 Hz), 8.70 (1H, dd, J=6, 2 Hz), 7.95(1H, dd, J=8, 6 Hz), 7.79–7.89(3H, m), 7.47–7.59(3H, m), 7.28–7.39(3H, m), 2.34(3H, s)
IR (KBr) cm⁻¹: 1658, 1620, 1551
Elemental analysis (%): $C_{22}H_{17}N_3O_3$
Calcd.: C 71.15, H 4.61, N 11.30.
Found: C 71.31, H 4.42, N 11.25.

EXAMPLE 11

4-Hydroxy-N-(3-nitrophenyl)-2-oxo-1-phenyl-1H-1,8-naphthyridine-3-carboxamide (Compound 11)

Compound 11 was obtained in the same manner as in Example 1 except for the use of 3-nitroaniline instead of n-butylamine (yield 77%).

Melting point: >300° C. (dimethylsulfoxide-water)
MS (EI) m/e 402(M⁺), 265, 263
NMR (CF₃COOD) δ (ppm): 9.45(1H, dd, J=8, 2 Hz), 8.76 (1H, t, J=2 Hz), 8.71(1H, dd, J=6, 2 Hz), 8.24(1H, dd, J=8, 2 Hz), 7.91–7.99(2H, m), 7.80–7.87(3H, m), 7.69(1H, t, J=8 Hz), 7.54–7.58(2H, m)
IR (KBr) cm⁻¹: 1660, 1548
Elemental analysis (%): $C_{21}H_{14}N_4O_5$
Calcd.: C 62.69, H 3.51, N 13.92.
Found: C 62.97, H 3.09, N 13.87.

EXAMPLE 12

4-Hydroxy-2-oxo-1-phenyl-N-(2-thiazolyl)-1H-1,8-naphthyridine-3-carboxamide (Compound 12)

Compound 12 was obtained in the same manner as in Example 1 except for the use of 2-aminothiazole instead of n-butylamine (yield 81%).

Melting point: >300° C. (dimethylformamide-water)
MS (EI) m/e: 364(M⁺), 265, 100
NMR (CF₃COOD) δ (ppm): 9.48(1H, dd, J=8, 2 Hz), 8.78 (1H, dd, J=6, 2 Hz), 8.01(1H, dd, J=8, 6 Hz), 8.77–8.90(4H, m), 7.62(1H, d, J=4 Hz), 7.52–7.56(2H, m)
IR (KBr) cm⁻¹: 1652, 1620, 1547
Elemental analysis (%): $C_{18}H_{12}N_4O_3S$
Calcd.: C 59.33, H 3.32, N 15.38.
Found: C 59.76, H 3.00, N 15.57.

EXAMPLE 13

N-(2-Benzothiazolyl)-4-hydroxy-2-oxo-1-phenyl-1H-1,8-naphthyridine-3-carboxamide (Compound 13)

Compound 13 was obtained in the same manner as in Example 1 except for the use of 2-aminobenzothiazole instead of n-butylamine (yield 51%).

Melting point: >300° C. (dimethylformamide-water)
MS (EI) m/e: 414(M⁺), 265, 150
NMR (CF₃COOD) δ (ppm): 9.49(1H, dd, J=8, 2 Hz), 8.80 (1H, dd, J=6, 2 Hz), 8.12(1H, d, J=8 Hz), 8.03(1H, dd, J=8, 6 Hz), 7.75–7.97(6H, m), 7.53–7.61(2H, m)
IR (KBr) cm 1658, 1616, 1532
Elemental analysis (%): $C_{22}H_{14}N_4O_3S$
Calcd.: C 63.76, H 3.40, N 13.52.
Found: C 63.59, H 3.01, N 13.21.

EXAMPLE 14

N-(4-Chlorophenyl)-4-hydroxy-2-oxo-1-phenyl-1H-1,8-naphthyridine-3-carboxamide (Compound 14)

Dimethylsulfoxide (20 ml) and 0.92 ml (0.0066 mol) of triethylamine were added to 1.5 g (0.0063 mol) of Compound IXa obtained in Reference Example 3 and 0.85 ml (0.006 mol) of 4-chlorophenyl isocyanate, and the mixture was stirred overnight. The mixture was poured into 150 ml of 4N aqueous solution of hydrochloric acid, and the precipitate was taken by filtration and then added to 150 ml of ethyl acetate. The mixture was stirred for 30 minutes and the crystals were taken by filtration. Recrystallization from dimethylsulfoxide-water gave 1.4 g (yield 56%) of Compound 14 as colorless crystals.

Melting point: 281–286° C. (dimethylsulfoxide-water)
MS (EI) m/e: 391(M−), 265, 127
NMR (CF$_3$COOD) δ (ppm): 9.43(1H, dd, J=8, 2 Hz), 8.69 (1H, dd, J=6, 2 Hz), 7.94(1H, dd, J=8, 4 Hz), 7.78–7.87(3H, m), 7.42–7.59(6H, m)
IR (KBr) cm$^{-1}$: 1660, 1593, 1548
Elemental analysis (%): C$_{21}$H$_{14}$ClN$_3$O$_3$
Calcd.: C 64.38, H 3.60, N 10.72.
Found: C 64.19, H 3.57, N 10.52.

EXAMPLE 15

4-Hydroxy-N-(4-nitrophenyl)-2-oxo-1-phenyl-1H-1,8-naphthyridine-3-carboxamide (Compound 15)

Compound 15 was obtained in the same manner as in Example 14 except for the use of 4-nitrophenyl isocyanate instead of 4-chlorophenyl isocyanate (yield 42%).

Melting point: >300° C. (dimethylsulfoxide-water)
MS (EI) m/e: 402(M+), 265, 77
NMR (CF$_3$COOD) δ (ppm): 9.45(1H, dd, J=8, 2 Hz), 8.74 (1H, dd, J=6, 2 Hz), 8.39(2H, d, J=9 Hz), 7.80–8.01 (6H, m), 7.50–7.67(2H, m)
IR (KBr) cm$^{-1}$: 1659, 1548, 1511

EXAMPLE 16

4-Hydroxy-N-(4-methoxyphenyl)-2-oxo-1-phenyl-1H-1,8-naphthyridine-3-carboxamide (Compound 16)

Compound 16 was obtained in the same manner as in Example 14 except for the use of 4-methoxyphenyl isocyanate instead of 4-chlorophenyl isocyanate (yield 42%).

Melting point: >300° C. (dimethylsulfoxide-water)
MS (EI) m/e: 387(M+), 265, 123
NMR (CF$_3$COOD) δ (ppm): 9.43(1H, dd, J=8, 2 Hz), 8.69 (1H, dd, J=6, 2 Hz), 7.94(1H, dd, J=8, 6 Hz), 7.80–7.92(3H, m), 7.45–7.66(4H, m), 7.08–7.23 (2H, m)
IR (KBr) cm$^{-1}$: 1657, 1602, 1554
Elemental analysis (%): C$_{22}$H$_{17}$N$_3$O$_4$
Calcd.: C 68.21, H 4.42, N 10.84.
Found: C 68.18, H 4.46, N 10.80.

EXAMPLE 17

4-Hydroxy-N-(4-methylphenyl)-2-oxo-1-phenyl-1H-1,8-naphthyridine-3-carboxamide (Compound 17)

Compound 17 was obtained in the same manner as in Example 14 except for the use of 4-methylphenyl isocyanate instead of 4-chlorophenyl isocyanate (yield 45%).

Melting point: >300° C. (dimethylsulfoxide-water)
MS (EI) m/e: 371(M+), 265, 107
NMR (CF$_3$COOD) δ (ppm): 9.43(1H, dd, J=8, 2 Hz), 8.68 (1H, dd, J=6, 2 Hz), 7.94(1H, dd, J=8, 6 Hz), 7.76–7.91(3H, m), 7.50–7.64(2H, m), 7.27–7.41 (4H, m), 2.40(3H, s)
IR (KBr) cm$^{-1}$: 1658, 1598, 1550
Elemental analysis (%): C$_{22}$H$_{17}$N$_3$O$_3$
Calcd.: C 71.14, H 4.61, N 11.31.
Found: C 70.83, H 4.64, N 11.17.

EXAMPLE 18

4-Hydroxy-N-(3-methoxyphenyl)-2-oxo-1-phenyl-1H-1,8-naphthyridine-3-carboxamide (Compound 18)

Compound 18 was obtained in the same manner as in Example 14 except for the use of 3-methoxyphenyl isocyanate instead of 4-chlorophenyl isocyanate (yield 48%).

Melting point: 275–280° C. (dimethylsulfoxide-water)
MS (EI) m/e: 387(M−), 265, 123
NMR (CF$_3$COOD) δ (ppm): 9.44(1H, dd, J=8, 2 Hz), 8.69 (1H, dd, J=6, 2 Hz), 7.94(1H, dd, J=8, 6 Hz), 7.78–7.90(4H, m), 7.32–7.62(5H, m), 4.04(3H, s)
IR (KBr) cm$^{-1}$: 1656, 1593, 1549
Elemental analysis (%): C$_{22}$H$_{17}$N$_3$O$_4$
Calcd.: C 68.21, H 4.42, N 10.85.
Found: C 67.81, H 4.39, N 10.80.

EXAMPLE 19

4-Hydroxy-N-(2-methoxyphenyl)-2-oxo-1-phenyl-1H-1,8-naphthyridine-3-carboxamide (Compound 19)

Compound 19 was obtained in the same manner as in Example 14 except for the use of 2-methoxyphenyl isocyanate instead of 4-chlorophenyl isocyanate (yield 52%).

Melting point: >300° C. (dimethylsulfoxide-water)
MS (EI) m/e: 387(M+), 265, 123
NMR (CF$_3$COOD) δ (ppm): 9.45(1H, dd, J=8, 2 Hz), 8.67 (1H, dd, J=6, 2 Hz), 7.78–8.09(5H, m), 7.50–7.69 (2H, m), 7.34(1H, t, J=8 Hz), 7.04–7.20(2H, m), 3.94(3H, s)
IR (KBr) cm$^{-1}$: 1600, 1577, 1548
Elemental analysis (%): C$_{22}$H$_{17}$N$_3$O$_4$·0.1H$_2$O
Calcd.: C 67.89, H 4.45, N 10.80.
Found: C 67.78, H 4.43, N 10.64.

EXAMPLE 20

4-Hydroxy-2-oxo-1,N-diphenyl-1H-1,8-naphthyridine-3-carboxamide (Compound 20)

Compound 20 was obtained in the same manner as in Example 14 except for the use of phenyl isocyanate instead of 4-chlorophenyl isocyanate (yield 50%).

Melting point: >300° C. (dimethylsulfoxide-water)
MS (EI) m/e: 357(M+), 265, 197
NMR (CF$_3$COOD) δ (ppm): 9.44(1H, dd, J=8, 2 Hz), 8.69 (1H, dd, J=6, 2 Hz), 7.78–8.02(4H, m), 7.32–7.68 (7H, m)
IR (KBr) cm$^{-1}$: 1663, 1598, 1548
Elemental analysis (%): C$_{21}$H$_{15}$N$_3$O$_3$
Calcd.: C 70.58, H 4.23, N 11.75.
Found: C 70.31, H 4.13, N 11.46.

EXAMPLE 21

N-(1-Benzylpiperidin-4-yl)-4-hydroxy-2-oxo-1-phenyl-1H-1,8-naphthyridine-3-carboxamide (Compound 21)

Compound 21 was obtained in the same manner as in Example 1 except for the use of 4-amino-1-benzylpiperidine instead of n-butylamine (yield 97%).

Melting point: 205–206° C. (ethanol-methanol)
MS (EI) m/e: 454(M+), 265, 91, 82
NMR (CF$_3$COOD) δ (ppm): 9.41(1H, dd, J=8, 2 Hz), 8.65 (1H, dd, J=6, 2 Hz), 7.94(1H, t, J=7 Hz), 7.77–7.90 (3H, m), 7.42–7.64(7H, m), 4.42(2H, s), 3.86(2H, d, J=12 Hz), 3.42–3.73(1H, m), 3.30(2H, t, J=12 Hz), 2.47(2H, d, J=12 Hz), 2.07–2.25(2H, m)
Elemental analysis (%): C$_{27}$H$_{20}$N$_4$O$_3$
Calcd.: C 71.35, H 5.77, N 12.33.
Found: C 71.38, H 5.95, N 12.52.

EXAMPLE 22

4-Hydroxy-2-oxo-1-phenyl-N-(thiazolin-2-yl)-1H-1,8-naphthyridine-3-carboxamide (Compound 22)

Compound 22 was obtained in the same manner as in Example 1 except for the use of 2-aminothiazoline instead of n-butylamine (yield 71%).

Melting point: >300° C. (xylene)
MS (EI) m/e: 366(M+), 347
IR (KBr) cm$^{-1}$: 1701, 1593, 1549
NMR (CF$_3$COOD) δ (ppm): 9.79(1H, dd, J=8, 2 Hz), 8.64 (1H, dd, J=6, 2 Hz), 7.93(1H, t, J=7 Hz), 7.75-7.87 (3H, m), 7.45-7.58(2H, m), 4.85(2H, t, J=8 Hz), 3.78(2H, t, J=8 Hz)
Elemental analysis (%): C$_{18}$H$_{14}$N$_4$O$_3$S.0.2H$_2$O
Calcd.: C 58.43, H 3.92, N 15.14.
Found: C 58.36, H 3.64, N 14.87.

EXAMPLE 23

4-Hydroxy-2-oxo-1-phenyl-N-(pyrazin-2-yl)-1H-1,8-naphthyridine-3-carboxamide (Compound 23)

Compound 23 was obtained in the same manner as in Example 1 except for the use of 2-aminopyrazine instead of n-butylamine (yield 38%).

Melting point: >300° C. (xylene)
MS (EI) m/e: 359(M+), 263
IR (KBr) cm$^{-1}$: 1659, 1621, 1520
NMR (CF$_3$COOD) δ (ppm): 9.92(1H, s), 9.48(1H, dd, J=8, 2 Hz), 9.25(1H, dd, J=3, 1 Hz), 8.72-8.74(2H, m), 8.74(1H, t, J=7 Hz), 7.78-7.88(3H, m), 7.50-7.60 (2H, m)
Elemental analysis (%): C$_{19}$H$_{13}$N$_5$O$_3$
Calcd.: C 63.51, H 3.65, N 19.49.
Found: C 63.68, H 3.39, N 19.19.

EXAMPLE 24

4-Hydroxy-2-oxo-1-phenyl-N-(5-ethyl-1,3,4-thiadiazol-2-yl)-1H-1,8-naphthyridine-3-carboxamide (Compound 24)

Compound 24 was obtained in the same manner as in Example 1 except for the use of 2-amino-5-ethyl-1,3,4-thiadiazole instead of n-butylamine (yield 68%).

Melting point: >298° C. (DMF-water)
MS (EI) m/e: 393(M+), 265, 263
IR (KBr) cm$^{-1}$: 1660, 1530, 1471
NMR (CF$_3$COOD) δ (ppm): 9.46(1H, dd, J=8, 2 Hz), 8.77 (1H, dd, J=6, 2 Hz), 8.10(1H, t, J=7 Hz), 7.78-7.92 (3H, m), 7.50-7.58(2H, m), 3.46(2H, q, J=7 Hz), 1.67(3H, t, J=7 Hz)
Elemental analysis (%): C$_{19}$H$_{15}$N$_5$O$_3$S
Calcd.: C 58.00, H 3.84, N 17.80.
Found: C 58.16, H 3.59, N 17.58.

EXAMPLE 25

4-Hydroxy-N-(2-methoxypyridin-5-yl)-2-oxo-1-phenyl-1H-1,8-naphthyridine-3-carboxamide (Compound 25)

Compound 25 was obtained in the same manner as in Example 1 except for the use of 5-amino-2-methoxypyridine instead of n-butylamine (yield 71%).

Melting point: 285-287° C. (DMF-water)
MS (EI) m/e: 388(M+), 265, 124
IR (KBr) cm$^{-1}$: 1661, 1544, 1493
NMR (CF$_3$COOD) δ (ppm): 9.44(1H, d, J=4 Hz), 9.23(1H, brs), 8.71-8.80(2H, m), 7.80-8.01(4H, m), 7.51-7.60(3H, m), 4.34(3H, s)
Elemental analysis (%): C$_{21}$H$_{16}$N$_4$O$_4$.0.4H$_2$O
Calcd.: C 63.76, H 4.28, N 14.17.
Found: C 63.71, H 3.99, N 14.07.

EXAMPLE 26

N-(2-Chloropyridin-5-yl)-4-hydroxy-2-oxo-1-phenyl-1H-1,8-naphthyridine-3-carboxamide (Compound 26)

Compound 26 was obtained in the same manner as in Example 1 except for the use of 5-amino-2-chloropyridine instead of n-butylamine (yield 64%).

Melting point: 282-283° C. (chloroform)
MS (EI) m/e: 392(M+), 265, 128
IR (KBr) cm$^{-1}$: 1662, 1542, 1460
NMR (CF$_3$COOD) δ (ppm): 9.69(1H, brs), 9.46(1H, dd, J=8, 2 Hz), 8.88(1H, dd, J=6, 2 Hz), 8.72(1H, d, J=6 Hz), 8.07(1H, d, J=10 Hz), 7.97(1H, t, J=7 Hz), 7.82-7.86(3H, m), 7.52-7.57(2H, m)
Elemental analysis (%): C$_{20}$H$_{13}$N$_4$O$_3$Cl
Calcd.: C 61.16, H 3.34, N 14.26.
Found: C 60.98, H 3.32, N 14.15.

EXAMPLE 27

4-Hydroxy-N-morpholino-2-oxo-1-phenyl-1H-1,8-naphthyridine-3-carboxamide (Compound 27)

Compound 27 was obtained in the same manner as in Example 1 except for the use of N-aminomorpholine instead of n-butylamine (yield 87%).

Melting point: 263-266° C. (xylene)
MS (EI) m/e: 366(M+), 263, 102
IR (KBr) cm$^{-1}$: 1618, 1473, 1440, 1113
NMR (CF$_3$COOD) δ (ppm): 9.42(1H, dd, J=8, 2 Hz), 8.76 (1H, dd, J=6, 2 Hz), 7.98(1H, t, J=7 Hz), 7.80-7.86 (3H, m), 7.48-7.53(2H, m)
Elemental analysis (%): C$_{19}$H$_{18}$N$_4$O$_4$
Calcd.: C 62.29, H 4.59, N 15.29.
Found: C 62.46, H 4.80, N 15.40.

EXAMPLE 28

4-Hydroxy-2-oxo-1-phenyl-N-(4-pyridylmethyl)-1H-1,8-naphthyridine-3-carboxamide (Compound 28)

Compound 28 was obtained in the same manner as in Example 1 except for the use of 4-aminomethylpyridine instead of n-butylamine (yield 73%).

Melting point: 232-234° C. (xylene)
MS (EI) m/e: 372(M+), 263, 238, 108
IR (KBr) cm$^{-1}$: 1660, 1626, 1535
NMR (CF$_3$COOD) δ (ppm): 9.42(1H, dd, J=8, 2 Hz), 8.81 (1H, d, J=6 Hz), 8.69(1H, dd, J=6, 2 Hz), 8.17(1H, d, J=6 Hz), 7.96(1H, t, J=7 Hz), 7.78-7.85(3H, m), 7.48-7.55(2H, m), 5.10(2H, s)
Elemental analysis (%): C$_{21}$H$_{16}$N$_4$O$_3$
Calcd.: C 67.73, H 4.33, N 15.03.
Found C 67.74, H 4.27, N 14.89.

EXAMPLE 29

4-Hydroxy-2-oxo-1-phenyl-N-(3-pyridylmethyl)-1H-1,8-naphthyridine-3-carboxamide (Compound 29)

Compound 29 was obtained in the same manner as in Example 1 except for the use of 3-aminomethylpyridine instead of n-butylamine (yield 65%).

Melting point: 222-224° C. (xylene)
MS (EI) m/e: 372(M+), 263, 238, 108
IR (KBr) cm$^{-1}$: 1658, 1556
NMR (CF$_3$COOD) δ (ppm): 9.40(1H, dd, J=8, 2 Hz), 9.02 (1H, s), 8.76-8.83(2H, m), 8.64(1H, dd, J=6, 2 Hz), 8.14(1H, t, J=7 Hz), 7.92(1H, t, J=7 Hz), 7.78-7.86(3H, m), 7.47-7.55(2H, m), 5.02(2H, s)

Elemental analysis (%): C₂₁H₁₆N₄O₃
Calcd.: C 67.73, H 4.33, N 15.05.
Found: C 67.59, H 4.06, N 14.84.

EXAMPLE 30

N-(4-Aminophenyl)-4-hydroxy-2-oxo-1-phenyl-1H-1,8-naphthyridine-3-carboxamide (Compound 30)

Compound 30 was obtained in the same manner as in Example 1 except for the use of phenylenediamine instead of n-butylamine (yield 90%).

Melting point: >300° C. (xylene)
MS (EI) m/e: 372(M+), 108
IR (KBr) cm⁻¹: 1658, 1627, 1563, 1553, 1515
NMR (CF₃COOD) δ (ppm): 9.44(1H, dd, J=8, 2 Hz), 8.69 (1H, dd, J=6, 2 Hz), 7.73-7.96(6H, m), 7.53-7.65 (4H, m)
Elemental analysis (%): C₂₁H₁₆N₄O₃
Calcd.: C 67.73, H 4.33, N 15.04.
Found C 67.77, H 4.23, N 14.76.

EXAMPLE 31

4-Hydroxy-N-(3-methylpyridin-4-yl)-2-oxo-1-phenyl-1H-1,8-naphthyridine-3-carboxamide (Compound 31)

Compound 31 was obtained in the same manner as in Example 1 except for the use of 4-amino-3-methylpyridine instead of n-butylamine (yield 62%).

Melting point: 276-279° C. (DMF)
MS (EI) m/e: 372, 265, 263, 108
IR (KBr) cm⁻¹: 1666, 1594, 1434, 1394
Elemental analysis (%): C₂₁H₁₆N₄O₃·0.4H₂O
Calcd.: C 66.45, H 4.46, N 14.76.
Found: C 66.43, H 4.32, N 14.79.

EXAMPLE 32

4-Hydroxy-2-oxo-1-phenyl-N-(2-pyridyl)-1H-1,8-naphthyridine-3-carboxamide (Compound 32)

In 40 ml of N,N-dimethylacetamide was dissolved 1.9 g (0.0092 mol) of 2-ethoxycarbonyl-N-(2-pyridyl)acetamide, and 1.0 g (0.025 mol) of 60% sodium hydride was added to the solution under cooling. After evolution of hydrogen ceased, 2.0 g (0.0083 mol) of Compound Va obtained in Reference Example 1 was added in small portions to the mixture, followed by heating at 110° C. for one hour. The mixture was cooled and the solvent was evaporated under reduced pressure. Then, 50 ml of ethyl acetate and 50 ml of water were added to the residue, and the formed crystals were taken by filtration and dried. Recrystallization from N,N-dimethylformamide gave 0.88 g (yield 30%) of Compound 32 as light yellow crystals.

Melting point: >300° C. (DMF)
MS (EI) m/e: 358(M+), 263, 94
NMR (CF₃COOD) δ (ppm): 9.46(1H, dd, J=8, 2 Hz), 8.77 (1H, d, J=6 Hz), 8.55-8.65(2H, m), 7.98-8.06(2H, m), 7.81-7.92(4H, m), 7.52-7.58(2H, m)
IR (KBr) cm⁻¹: 1652, 1520, 1491, 1436
Elemental analysis (%): C₂₀H₁₄N₄O₃
Calcd.: C 67.03, H 3.94, N 15.63.
Found: C 67.07, H 3.85, N 15.34.

EXAMPLE 33

Tablets

Tablets, each having the following composition, are prepared in a conventional manner.

| | |
|---|---|
| Compound 1 | 50 mg |
| Lactose | 60 mg |
| Potato starch | 30 mg |
| Polyvinyl alcohol | 2 mg |
| Magnesium stearate | 1 mg |
| Tar pigment | trace |

EXAMPLE 34

Powder

Powder having the following composition is prepared in a conventional manner.

| | |
|---|---|
| Compound 2 | 50 mg |
| Lactose | 300 mg |

EXAMPLE 35

Syrup

Syrup having the following composition is prepared in a conventional manner.

| | |
|---|---|
| Compound 1 | 50 mg |
| Refined white sugar | 30 g |
| Ethyl p-hydroxybenzoate | 40 mg |
| Propyl p-hydroxybenzoate | 10 mg |
| Strawberry flavor | 0.1 cc |

Water is added to the composition to make the whole volume 100 cc.

EXAMPLE 36

Syrup

Syrup having the following composition is prepared in a conventional manner.

| | |
|---|---|
| Compound 2 | 50 mg |
| Refined white sugar | 30 g |
| Ethyl p-hydroxybenzoate | 40 mg |
| Propyl p-hydroxybenzoate | 10 mg |
| Strawberry flavor | 0.1 cc |

Water is added to the composition to make the whole volume 100 cc.

REFERENCE EXAMPLE 1

1-Phenyl-2H-pyrido[2,3-d][1,3]oxazine-2,4(1H)-dione (Compound Va)

In a mixture of 70 ml of 1,2-dichloroethane and 7 ml of dioxane was dissolved 7.0 g (0.031 mol) of methyl 2-anilinonicotinate [J. Org. Chem., 39, 1803 (1974)]. After 11 ml (0.092 mol) of trichloromethyl chloroformate was added dropwise to the solution at 60° C. with stirring, the mixture was refluxed for 3 hours. The mixture was slightly cooled and 0.25 g of activated carbon was added thereto, followed by refluxing for further 30 minutes in a nitrogen flow. The mixture was cooled to room temperature, filtered and concentrated. Recrystallization from methylene chloride-isopropyl ether gave 6.5 g (yield 87%) of Compound Va as colorless crystals.

Melting point: 196-198° C.
Elemental analysis (%): C₁₃H₈N₂O₃
Calcd.: C 65.00, H 3.36, N 11.66.

Found: C 65.11, H 3.22, N 11.48.
IR (KBr) νmax (cm$^{-1}$): 1791, 1727, 1584
NMR (CDCl$_3$) δ (ppm): 8.58(1H, dd, J=5, 2 Hz), 8.48(1H, dd, J=8, 2 Hz), 7.51-7.63(3H, m), 7.33-7.37(2H, m), 7.29(1H, dd, J=8, 5 Hz)
MS (m/z): 240(M$^+$), 196, 168

REFERENCE EXAMPLE 2

3-Ethoxycarbonyl-4-hydroxy-1-phenyl-1,8-naphthyridin-2(1H)-one (Compound IIa)

To 25 ml of N,N-dimethylacetamide was added 25 ml (0.16 mol) of diethyl malonate, and 0.80 g (0.020 mol) of 60% sodium hydride was added to the mixture under ice cooling. After evolution of hydrogen ceased, 4.0 g (0.017 mol) of Compound Va obtained in Reference Example 1 was added to the reaction mixture. The temperature was gradually elevated and the mixture was heated at 150° C. for 2.5 hours. The mixture was then cooled and 100 ml of ethyl acetate was added. The precipitate was taken by filtration and dissolved in 100 ml of water. The solution was made acidic with conc. hydrochloric acid and the precipitated crystals were taken by filtration. The crystals were washed with water and dried under reduced pressure. Recrystallization from isopropyl alcohol-ethanol gave 4.3 g (yield 88%) of Compound IIa as colorless crystals.

Melting point: 247-252° C.
Elemental analysis (%): C$_{17}$H$_{14}$N$_2$O$_4$
Calcd.: C 65.80, H 4.55, N 9.03.
Found: C 66.05, H 4.35, N 8.98.
IR (KBr) νmax (cm$^{-1}$): 1670, 1615, 466
NMR (CF$_3$COOD) δ (ppm): 8.48(1H, dd, J=4, 2 Hz), 8.46 (1H, dd, J=8, 2 Hz), 7.38-7.56(3H, m), 7.32(1H, dd, J=8, 4 Hz), 7.21-7.26(2H, m), 4.32(2H, q, J=7 Hz), 1.28(3H, t, J=7 Hz)
MS (m/z): 310(M$^+$), 263, 77

REFERENCE EXAMPLE 3

4-Hydroxy-1-phenyl-1,8-naphthyridin-2(1H)-one (Compound IXa)

To 70 ml of 2N sodium hydroxide solution was added 2 g (0.068 mol) of Compound IIa obtained in Reference Example 2, and the mixture was heated to reflux for one hour. After cooling, 2N hydrochloric acid was added to neutralize the mixture. The precipitated crystals was taken by filtration and dried. Recrystallization from dimethylsulfoxide-water gave 1.4 g (yield 86%) of Compound IXa.

Melting poing: 300° C.
Elemental analysis (%): C$_{14}$H$_{10}$N$_2$O$_2$.0.2H$_2$O
Calcd.: C 69.52, H 4.33, N 11.58.
Found: C 69.28, H 3.99, N 11.53.
IR (KBr) νmax (cm$^{-1}$): 1680, 1641, 1615

NMR (CF$_3$COOD) δ (ppm): 11.79(1H, brs) 8.40(1H, dd, J=4, 2 Hz), 8.26(1H, dd, J=8, 2 Hz), 7.37-7.53(3H, m), 7.18-7.28(3H, m), 5.95(1H, s)
MS (m/z): 238(M$^+$), 237, 195, 77

What is claimed is:

1. A naphthyridine derivative represented by formula (I).

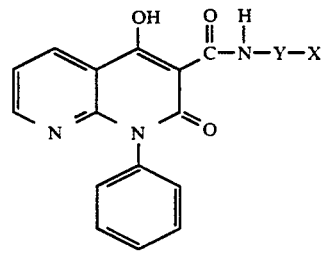

wherein:

X represents aryl which is optionally substituted with 1 or 2 substituents independently selected from the group consisting of lower alkyl, lower alkoxy, halogen, nitro and amino; aromatic heterocyclic group selected from the group consisting of pyridyl, pyrimidinyl, thiazolyl and benzothiazolyl which aromatic heterocyclic group is optionally substituted with 1 or 2 substituents independently selected from the group consisting of lower alkyl, lower alkoxy, halogen, nitro and amino;

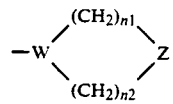

wherein W represents N or CH, Z represents a single bond, oxygen or NR$^3$ (wherein R$^3$ represents hydrogen, lower alkyl or benzyl) and n1 and n2 represent an integer of 1 to 3; or thiazolinyl which is optionally substituted with 1 or 2 substituents independently selected from the group consisting of lower alkyl, lower alkoxy, halogen, nitro and amino; and Y is a single bond or alkylene or a pharmaceutically acceptable salt thereof.

2. A compound according to claim 1, wherein said salt is an acid addition salt, a metal salt, an ammonium salt, an organic amine addition salt or an amino acid addition salt.

3. A pharmaceutical composition comprising a pharmaceutical carrier and, as an active ingredient, an effective amount of the compound as defined by claim 1.

* * * * *

UNITED STATES PATENT AND TRADEMARK OFFICE
CERTIFICATE OF CORRECTION

PATENT NO. : 5,126,341
DATED : June 30, 1992
INVENTOR(S) : FUMIO SUZUKI, ET AL.

Page 1 of 2

It is certified that error appears in the above-identified patent and that said Letters Patent is hereby corrected as shown below:

Title page:

IN [56] REFERENCES CITED

Under U.S. PATENT DOCUMENTS,

"4,264,602  4/1961  Hardtmann" should read
--4,264,602  4/1981  Hardtmann--.

Under U.S. PATENT DOCUMENTS, insert:
--4,128,649  12/1978  Hardtmann
 3,591,584   7/1971  Lombardino
 4,215,123   7/1980  Scotese--.

After U.S. PATENT DOCUMENTS, insert:

--    FOREIGN PATENT DOCUMENTS 92786   11/1983  EPO.
    267740   5/1988  EPO.
    36694    1977    Japan.

OTHER PUBLICATIONS

J. Med. Chem., Vol. 31, No. 7, p. 1453 (1988);
J. Pharm. Exp. Ther., Vol. 246, p. 578 (1988);
J. Med. Chem., Vol. 30, No. 12, p. 2270 (1987) --.

COLUMN 11

Line 20, "iment" should read --iment.--.

UNITED STATES PATENT AND TRADEMARK OFFICE
CERTIFICATE OF CORRECTION

PATENT NO. : 5,126,341
DATED : June 30, 1992
INVENTOR(S) : FUMIO SUZUKI, ET AL.

Page 2 of 2

It is certified that error appears in the above-identified patent and that said Letters Patent is hereby corrected as shown below:

COLUMN 13

Line 10, "atone" should read --at one--.
Line 51, "IR (KBr) cm$^{31\ 1}$" should read --IR (KBr) cm$^{-1}$--.
Line 54, "N 14.184." should read --N 14.18.--.

COLUMN 16

Line 50, "IR (KBr) cm 1658" should read
--IR (KBr) cm$^{-1}$: 1658--.

COLUMN 23

Line 46, "was" should read --were--.

Signed and Sealed this

Thirtieth Day of November, 1993

Attest:

BRUCE LEHMAN

Attesting Officer

Commissioner of Patents and Trademarks